United States Patent
Kaplan et al.

(10) Patent No.: US 8,568,319 B1
(45) Date of Patent: Oct. 29, 2013

(54) ULTRASOUND IMAGING SYSTEM APPARATUS AND METHOD WITH ADC SATURATION MONITOR

(76) Inventors: Mitchell Kaplan, Lake Forest Park, WA (US); Andrew Lundberg, Woodinville, WA (US); Thomas M. Duffy, Snohomish, WA (US)

( * ) Notice: Subject to any disclaimer, the term of this patent is extended or adjusted under 35 U.S.C. 154(b) by 899 days.

(21) Appl. No.: 12/704,397

(22) Filed: Feb. 11, 2010

(51) Int. Cl.
*A61B 8/00* (2006.01)

(52) U.S. Cl.
USPC .............................. 600/437; 600/407; 600/459

(58) Field of Classification Search
USPC ...................... 600/407, 437, 459; 73/618–631
See application file for complete search history.

(56) References Cited

U.S. PATENT DOCUMENTS

| | | | |
|---|---|---|---|
| 4,324,258 A * | 4/1982 | Huebscher et al. | 600/455 |
| 5,005,419 A * | 4/1991 | O'Donnell et al. | 73/626 |
| 5,197,477 A | 3/1993 | Peterson et al. | |
| 5,722,412 A | 3/1998 | Pflugrath et al. | |
| 5,817,024 A | 10/1998 | Ogle et al. | |
| 5,893,363 A | 4/1999 | Little et al. | |
| 6,383,139 B1 | 5/2002 | Hwang et al. | |
| 6,471,651 B1 | 10/2002 | Hwang et al. | |
| 6,648,826 B2 | 11/2003 | Little et al. | |
| 7,604,596 B2 | 10/2009 | Hwang et al. | |
| 2005/0228287 A1 | 10/2005 | Little et al. | |
| 2007/0071266 A1 | 3/2007 | Little et al. | |
| 2008/0287789 A1 | 11/2008 | Hwang et al. | |
| 2009/0069681 A1 | 3/2009 | Lundberg et al. | |
| 2009/0069725 A1 | 3/2009 | Diener et al. | |
| 2009/0275835 A1 | 11/2009 | Hwang et al. | |

* cited by examiner

*Primary Examiner* — Peter Luong
(74) *Attorney, Agent, or Firm* — Perkins Coie LLP

(57) ABSTRACT

An ultrasound imaging system and method employs hardware and/or software to monitor values indicative of analog-to-digital converter (ADC) saturation for each channel as a function of depth. Any of a number of actions may be performed based on the monitored values. For example, analog amplification or TGC may be adjusted to enhance the use of a dynamic range of ADCs while reducing or eliminating ADC saturation. A TGC profile may be adjusted. An alert may be provided. A power consumption may be adjusted.

34 Claims, 12 Drawing Sheets

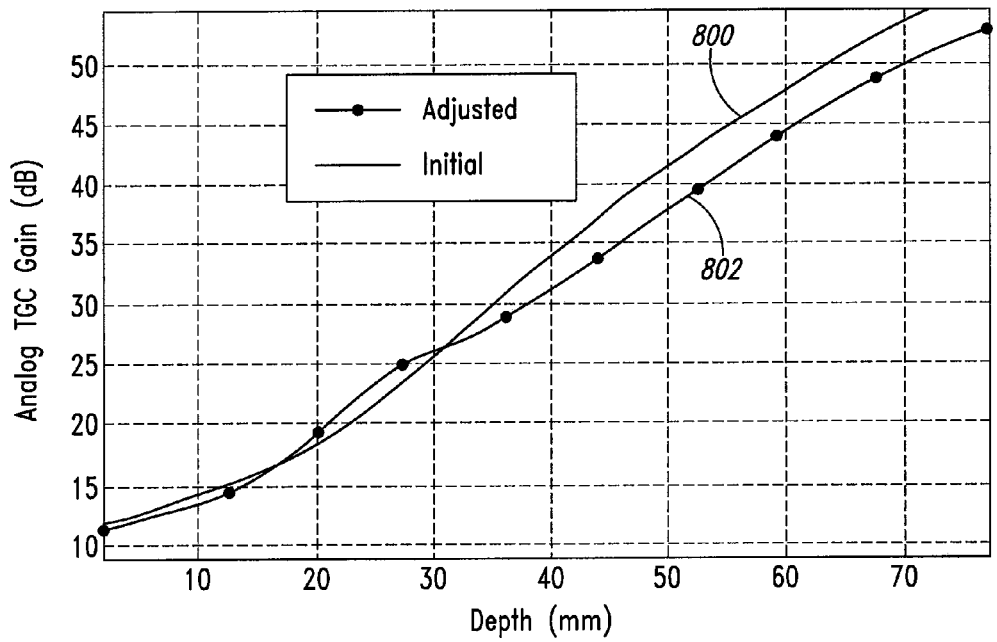

*FIG. 8*

```
                                                        ┌─ 900
    ┌─────────────────────────────────────────────────┐
    │ FOR EACH OF A PLURALITY OF RANGES OF DEPTHS INCREMENT │
    │   RESPECTIVE COUNTER FOR THE RANGE OF DEPTHS FOR THE  │
    │   CHANNEL EACH TIME SATURATION MONITORING THRESHOLD IS │──── 902
    │   ENCOUNTERED AT THE RESPECTIVE RANGE OF DEPTHS FOR   │
    │                      THE CHANNEL                      │
    └─────────────────────────────────────────────────┘
```

*FIG. 9*

INCREMENT COMMON COUNTER FOR THE RESPECTIVE RANGE OF DEPTH EACH TIME SATURATION MONITORING THRESHOLD IS ENCOUNTERED AT THE RESPECTIVE RANGE OF DEPTHS FOR ANY OF THE CHANNELS

ULTRASOUND IMAGING SYSTEM APPARATUS AND METHOD WITH ADC SATURATION MONITOR

BACKGROUND

1. Technical Field

This application relates to ultrasound imaging systems, for instance medical ultrasound diagnostic imaging systems and, in particular, to processing return or echo signals in ultrasound imaging systems.

2. Description of the Related Art

Ultrasound imaging systems employ transducer arrays to produce and transmit ultrasound into a body, tissue or other material. The transducer arrays also receive ultrasound returns or echoes and produce analog transducer element voltage signals which are induced at the transducer array by the received ultrasound returns or echoes. Ultrasound imaging systems typically use amplifiers to amplify the analog transducer element voltage signals before digitization. The analog amplification may vary with imaging depth (i.e., time gain compensation or control, i.e., TGC) to compensate for attenuation of ultrasound with depth.

Ultrasound imaging systems typically employ analog-to-digital converters (ADCs) to digitize the amplified analog transducer element voltage signals. Often a separate ADC is used for each analog channel, the ADCs mapped to the transducer elements of the transducer array. Appropriate focus delays may be applied before the digitized ADC output values from the channels are summed to form beams that are ultimately used to produce image data.

To reduce system cost and power consumption, the ADCs often limit the number of bits (e.g., 12 bits) used to digitize the transducer element voltage signals. The amplifiers are typically set so that a peak signal input to the ADC is close to a maximum range of the ADC (i.e., ADC output is close to a maximum possible digital value) in order to best discriminate the ultrasound signal from noise and to make maximum use of the dynamic range of the ADC (i.e., use as many of the available digital values as possible to represent the varying ultrasound signal). However, if saturation occurs (i.e., ADC values saturate at the maximum value of ADC), the ultrasound image is often significantly degraded, for example by distortion, artifacts, clipping, etc. Thus, the settings for the analog amplification are typically a compromise between a cost associated with a signal that is too low (i.e., small dynamic range and decreased signal-to-noise ratio) and the risk of encountering or exceeding a signal that is too high (e.g., clipping).

Typically, a single setting is used for the analog amplification, which setting must accommodate a broad variety of imaging conditions (e.g., varying patients, different anatomy, etc.). Consequently, a significant amount of the total dynamic range is sacrificed to avoid ADC saturation. It is not possible to reliably detect saturation after summing the individual channel contributions because it is possible, and in fact likely, that only some of the ADC channels actually saturate while other ADC channels do not. Thus, the beam sums are typically well below the maximum possible sum (i.e., maximum ADC value per channel times the number of channels).

New approaches that address at least some of the above described saturation issues are desirable.

BRIEF SUMMARY

A system and method employing hardware and/or software monitors values indicative of analog-to-digital converter (ADC) saturation for each channel as a function of depth and performs some action in response. For example, the system and method may adjust analog amplification or TGC in response to monitored values. For instance, analog amplification or TGC may be adjusted to increase use of a dynamic range of ADCs while reducing or eliminating ADC saturation. Also for example, an alert may be provided to via a user interface of the ultrasound imaging system, a time gain compensation or control profile may be adjusted, and/or a power state may be changed or adjusted.

A method of operating an ultrasound imaging system may be summarized as including, for each of a plurality of channels of the ultrasound imaging system, monitoring by at least one component of the ultrasound imaging system at least one respective value that is indicative of an analog-to-digital conversion saturation condition for the channel as a function of depth; and performing at least one action at least partially in response to the monitoring of the at least one respective value that is indicative of an analog-to-digital conversion saturation condition for the channel as a function of depth.

Performing at least one action may include for at least one of the channels of the ultrasound imaging system, adjusting a gain of a depth dependent analog amplification of at least one return signal produced by at least one transducer element based at least in part on the monitoring.

Adjusting a gain of a depth dependent analog amplification of at least one analog return signal may include adjusting the gain of the depth dependent analog amplification of the at least one analog return signal to at least reduce occurrences of saturation in the analog-to-digital conversion of the at least one analog return signal.

Adjusting a gain of a depth dependent analog amplification of at least one analog return signal may include adjusting the gain of the depth dependent analog amplification of the at least one analog return signal to prevent saturation in the analog-to-digital conversion of the at least one analog return signal.

Adjusting a gain of a depth dependent analog amplification of at least one analog return signal may include adjusting the gain of the depth dependent analog amplification of the at least one analog return signal to increase occurrences of saturation in the analog-to-digital conversion of the at least one analog return signal.

Monitoring at least one respective value that is indicative of an analog-to-digital conversion saturation condition for the channel as a function of depth may include monitoring an analog-to-digital conversion value resulting from an analog-to-digital conversion for the channel as a function of depth.

Monitoring an analog-to-digital conversion value resulting from an analog-to-digital conversion for the channel as a function of depth may include, for each of a plurality of ranges of depths setting a status bit in an analog-to-digital conversion saturation status register corresponding to a respective one of the ranges of depths if a saturation monitoring threshold value is encountered or exceeded at the respective one of the ranges of depths for the channel.

The range of depths may be programmable, and may further include modifying the range of depths for at least some of the channels based on at least one input received from a user.

The method may further include creating a bit mask; and applying the bit mask to selectively mask off portions of the analog-to-digital conversion saturation status register corresponding to respective ones of a plurality of transmit focal zones.

Monitoring an analog-to-digital conversion value resulting from an analog-to-digital conversion for the channel as a function of depth may include, for each of a plurality of ranges of depths incrementing a respective counter for the respective one of the ranges of depths for the channel each time a saturation monitoring threshold is encountered or exceeded at the respective one of the ranges of depths for the channel.

Monitoring an analog-to-digital conversion value resulting from an analog-to-digital conversion for the channel as a function of depth may include incrementing a respective common counter for the respective one of the ranges of depth each time a saturation monitoring threshold is encountered or exceeded at the respective one of the ranges of depths for any of the channels.

The saturation threshold may be user programmable, and may further include setting the saturation monitoring threshold based on at least one input received from a user. Monitoring an analog-to-digital conversion value resulting from an analog-to-digital conversion for the channel as a function of depth may include determining whether the analog-to-digital conversion value exceeds at least one of a maximum positive value or a maximum negative value of a respective analog-to-digital converter of the channel.

The method may further include summing a number of digitized return signals of a plurality of channels downstream of the monitoring of the analog-to-digital conversion value resulting from the analog-to-digital conversion for the channel as a function of depth.

Performing at least one action may include providing an alert to via a user interface of the ultrasound imaging system. Performing at least one action may include adjusting a time gain control profile. Performing at least one action may include providing a confidence metric for at least one automated image measurement. Performing at least one action may include changing a power consumption state of at least a portion of the ultrasound imaging system.

The method may further include for at least some of the channels, adjusting a digital amplification of a digitized return resulting from an analog-to-digital conversion of the at least one return signal to compensate for the adjusting of the gain of the depth dependent analog amplification.

An ultrasound system may be summarized as including an analog amplification stage operable to respectively amplify analog return signals produced by at least one transducer element on each of a plurality of channels of the ultrasound system; an analog-to-digital conversion stage operable to respectively convert the amplified analog return signals into digital return signals on each of the plurality of channels of the ultrasound system; an analog-to-digital conversion saturation monitor stage operable to monitor a respective value that is indicative of an analog-to-digital conversion saturation condition for each of the channels as a function of depth and to perform at least one action in response to the monitored values; and a digital processor stage operable to process the digital ultrasound return signals.

The analog-to-digital conversion saturation monitor stage may be configured to respectively adjust a gain in the analog amplification of the analog return signals produced by the analog amplification stage on each of the plurality of channels of the ultrasound system as a function of depth. The analog-to-digital conversion saturation monitor stage may be configured to adjust a gain in the analog amplification of the analog return signals produced by the analog amplification stage on each of the plurality of channels of the ultrasound system as a function of depth to at least reduce an occurrence of saturation of the analog-to-digital conversion by the analog-to-digital conversion stage. The analog-to-digital conversion saturation monitor stage may be further operable to adjust a gain in the analog amplification of the analog return signals produced by the analog amplification stage on each of the plurality of channels of the ultrasound system as a function of depth to increase an occurrence of saturation of the analog-to-digital conversion by the analog-to-digital conversion stage.

The analog-to-digital conversion saturation feedback stage may be further operable to adjust the gain in the analog amplification for the respective channels based at least in part on the detected respective values.

For each of the channels the analog-to-digital conversion saturation monitor stage may set a status bit in a respective analog-to-digital conversion saturation status register for the channel, the status bit corresponding to a respective one of a plurality of ranges of depths, if a saturation monitoring threshold value is exceeded at the respective one of the ranges of depths for the respective channel.

The analog-to-digital conversion saturation monitor stage may selectively mask off portions of the analog-to-digital conversion saturation status register corresponding to respective ones of a plurality of transmit focal zones with a bit mask.

For each of the channels the analog-to-digital conversion saturation monitor stage may increment a respective counter for a respective one of each of a plurality of ranges of depths each time a saturation monitoring threshold is exceeded at the respective one of the ranges of depths for the respective channel.

The analog-to-digital conversion saturation monitor stage may increment a respective common counter for the respective one of a plurality of ranges of depths each time a saturation monitoring threshold is exceeded at the respective one of the ranges of depths for any of the channels.

The digital processor stage may be communicatively coupled to receive a number of compensation signals from the analog-to-digital conversion saturation monitor stage indicative of an amount of compensation to compensate for the adjustment of the gain in the analog amplification of the analog return signals for each of the channels, and may be operable to amplify the digital return signals from the analog-to-digital conversion stage for each of the channels based at least in part on the compensation signals.

The analog-to-digital conversion saturation feedback stage may set a saturation monitoring threshold based on at least one input received from a user and may modify a range of depths for at least some of the channels based on at least one input received from a user.

The analog-to-digital conversion saturation monitor stage may be configured to cause an alert to be provided via a user interface of the ultrasound imaging system based at least in part on the monitored values. The analog-to-digital conversion saturation monitor stage may be configured to adjust a time gain control profile based at least in part on the monitored values. The analog-to-digital conversion saturation monitor stage may be configured to provide a confidence metric for at least one automated image measurement based at least in part on the monitored values. The analog-to-digital conversion saturation monitor stage may be configured to at least one of entering a low power state in response to a lack of saturation and entering a normal power state in response to a saturation based at least in part on the monitored values.

A subsystem for an ultrasound imaging system may be summarized as including at least one saturation condition detector configured to detect an analog-to-digital conversion saturation condition as a function of depth for at least one of each of a plurality of channels; and at least one analog amplification adjustor configured to provide at least one adjustment signal to at least one analog amplifier, the at least one adjustment signal indicative of an amount of adjustment in a gain in a depth dependent amplification of analog return signals to at least reduce an occurrence of saturation in an analog-to-digital conversion of the analog return signals.

The subsystem may further include at least one compensator configured to provide at least one compensation signal to at least one digital amplifier, which at least one compensation signal is indicative of an amount of compensation in an amplification of digitized return signals to compensation for the amount of adjustment in gain in the depth dependent amplification of the analog return signals.

For each channel the at least one saturation condition detector may be configured to, for each of a plurality of ranges of depths, set a status bit in an analog-to-digital conversion saturation status register corresponding to a respective one of the ranges of depths if a saturation monitoring threshold value is encountered or exceeded at the respective one of the ranges of depths for the respective channel.

For each channel the at least one saturation condition detector may be configured to, for each of a plurality of ranges of depths, increment a respective counter for the respective one of the ranges of depths each time a saturation monitoring threshold is encountered or exceeded at the respective one of the ranges of depths for the respective channel.

The at least one saturation condition detector may be configured to increment a respective common counter for the respective one of the ranges of depth each time a saturation monitoring threshold is encountered or exceeded at the respective one of the ranges of depths for any of the channels. The subsystem may further include the analog amplifier and the digital amplifier.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 8 is a graph of analog gain as a function of depth for an exemplary operation of an ultrasound imaging system employing 1) a saturation status based approach to controlling ADC saturation; and 2) employing without controlling ADC saturation.

FIG. 9 is a low level flow diagram of a method of monitoring an ADC value for each channel as a function of depth using a respective channel counter register for each channel according to one illustrated embodiment.

DETAILED DESCRIPTION

Figure 1:
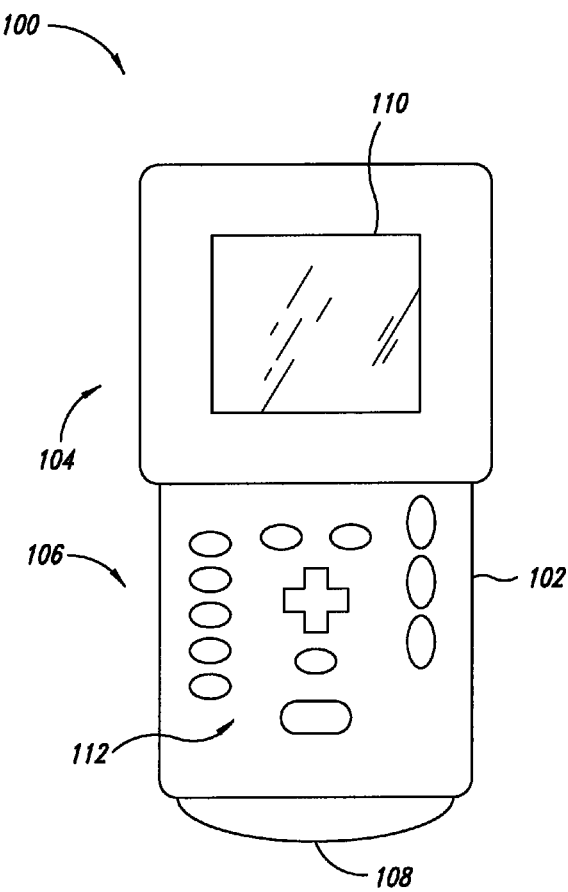
FIG. 1 is an isometric view of an ultrasound imaging system according to one illustrated embodiment, having a handheld form factor.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with ultrasound imaging systems, microprocessors, micro-controllers, application specific integrated circuits, transducers and displays have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

Various embodiments described herein employ hardware and/or software to enhance dynamic range and signal-to-noise ratio while controlling saturation of analog-to-digital converters or an analog-to-digital conversion function in ultrasound imaging systems. Such embodiments monitor values indicative of a saturation condition as a function of depth for each channel of an ultrasound imaging system and adjusts an amplification or gain in response to same.

In particular, the hardware and/or software may monitor an output value of each ADC (i.e., ADC value) as a function of depth. The hardware and/or software may, for example, set a status bit of a saturation status register corresponding to some range of depths for each channel if a saturation condition is encountered, met or exceeded in the respective range of depths. For example, the status bit may be set if a saturation threshold is encountered, met or exceeded. For instance, the status bit may be set if at least one of maximum positive or maximum negative ADC value is encountered, met or exceeded in the respective range of depths. The saturation condition threshold may be programmable or user configurable. The range of depths may be programmable or user configurable. A register with many (e.g., 16) bits may represent a full range of depths for a given analog channel/ADC. Alternatively, the hardware and/or software may increment a counter every time an ADC saturation threshold or value is encountered, met or exceeded, providing more detailed information about a severity or frequency of a saturation condition. Alternatively, the hardware and/or software may increment a counter corresponding to the total number of channels in saturation within each range of depths or depth-zone.

From time-to-time, the hardware and/or software reads the ADC saturation status registers or counters to analyze the ADC saturation condition as a function of depth and channel, and possibly other parameters such as ray index, focal zone, and mode (e.g., 2D echo versus Doppler). Based on the analysis, the hardware and/or software may perform any one or more actions. For example, the hardware and/or software may adjust a time gain compensation or depth-dependent analog gain (i.e., TGC) setting to more effectively utilize the ADC dynamic range without saturation. Thus, the hardware and/or software may for instance reduce gain at depths where excessive saturation is encountered, met or exceeded and possibly increase gain at other depths. The hardware and/or software may employ an algorithm that prevents oscillation and which approaches a stable operating point for a static imaging condition. An overall gain profile may be maintained by adjusting or compensating a digital gain to compensate for the adjustments made to analog gain. Also for example, the hardware and/or software may cause an alert (e.g., visual, aural, tactile) may be provided to via a user interface of the ultrasound imaging system. Such may allow a user to make an appropriate adjust, for example adjusting gain. As a further example, the hardware and/or software may adjust a defined time gain compensation profile. As an even further example, the hardware or software may be adjust a power consumption state of at least a portion of the ultrasound imaging system.

The approaches described herein may improve image quality by allowing the ultrasound imaging system to adjust the TGC while automatically adapting to current imaging conditions (e.g., patient body type, anatomy, etc.), rather than accepting the limitations and compromises required to accommodate a range of imaging conditions with a single TGC setting. Such may advantageously increase dynamic range, which improves image contrast resolution, as well as increase signal-to-noise ratio, which provides better penetration and spatial resolution, and may substantially reduce the likelihood of image degradation caused by saturation.

A number of illustrated embodiments are described below with reference to FIGS. 1-17.

FIG. 1 shows an ultrasound imaging system 100 according to one illustrated embodiment.

The ultrasound imaging system 100 may take the form of a portable or handheld ultrasound imaging system. For instance, the ultrasound imaging system 100 include a one piece or unitary housing 102 that has an upper section 104, a lower section 106, and a transducer array 108. The upper section 104 may include a display 110, for example a liquid crystal display (LCD). The lower section 106 may include a set of user controls 112. The display 110 and user controls 112 may form all or part of a user interface. The user controls 112 may allow a user to turn the ultrasound imaging system 1000N and OFF, enter time, date, and/or patient data, interact with a graphical user interface that includes user selectable icons or elements of a menu (e.g., pull down menu, popup menu), and/or select or set various operating characteristics such as an operating mode (e.g., B mode, Doppler), color Doppler sector or frame rate, and special functions. The transducer array 108 includes a set of ultrasound transducer elements which perform transformations between electrical signals and ultrasound, a physical aperture, and optionally a lens proximate the physical aperture. Suitable transducer arrays 108 are commercially available from a variety of manufacturers and/or suppliers. While illustrated as a single package, an ultrasound imaging system may be housed in two or more separate sections. Various suitable embodiments are described in U.S. Pat. No. 7,604,596. Other configurations of the ultrasound imaging system 100 may be employed.

Figure 2A:
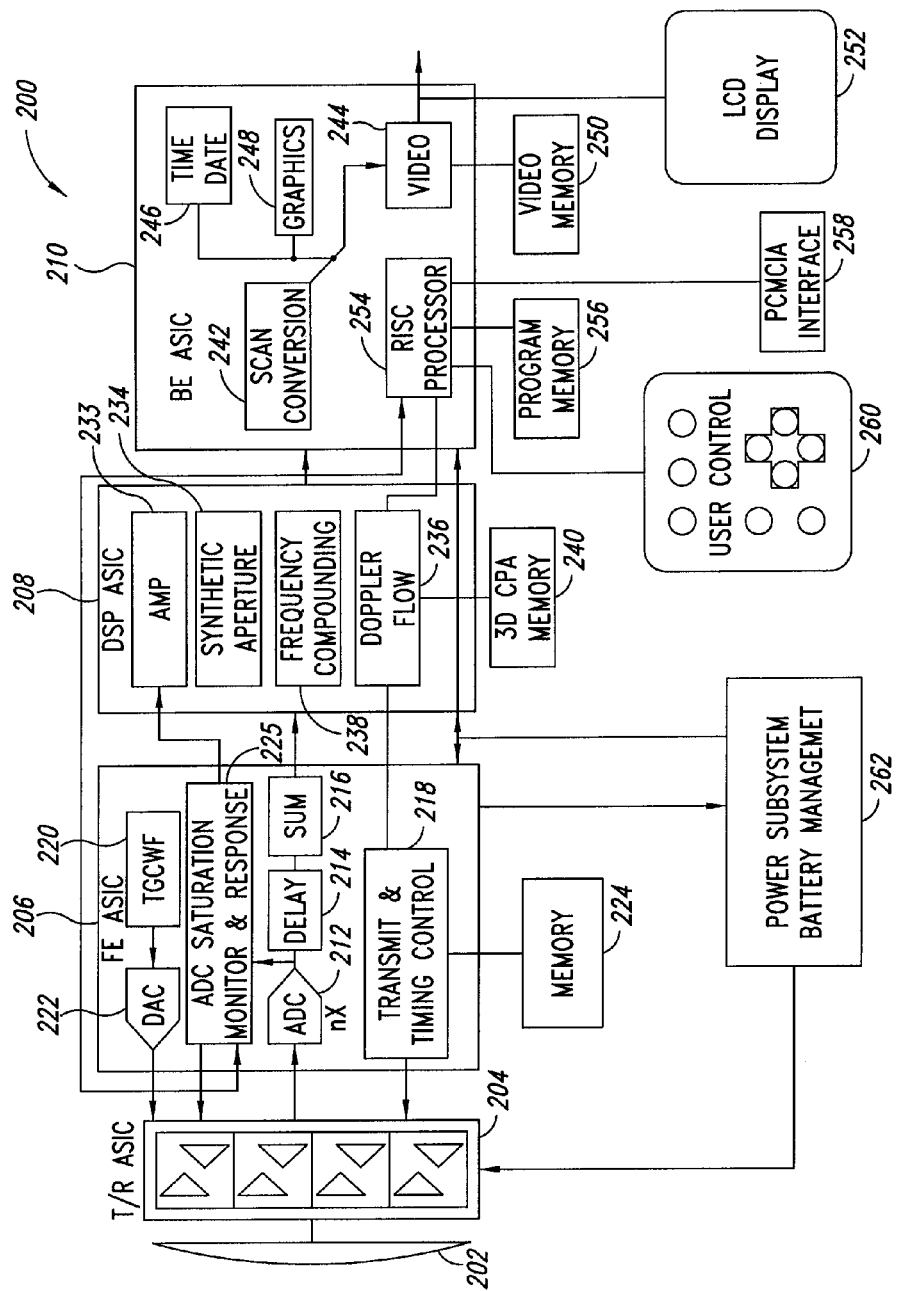
FIG. 2A is a schematic diagram of a system architecture of an ultrasound imaging system according to one illustrated embodiment.

FIG. 2A shows a system architecture 200 of an ultrasound imaging system according to one illustrated embodiment.

The system architecture includes a transducer array 202, transmit/receive application specific integrated circuit (ASIC) 204, front end ASIC 206, digital signal processor (DSP) ASIC 208, and backend ASIC 210, along with a number of other components and subsystems which are discussed below. The transducer array 202, transmit/receive ASIC 204, front end ASIC 206, DSP ASIC 208, backend ASIC 210, as well as the components and subsystems are coupled by one or more communications paths or buses. For example, the transducer array 202, transmit/receive ASIC 204, front end ASIC 206, DSP ASIC 208, backend ASIC 210 may be coupled by one or more data buses, instructions buses, and/or power buses. Such paths or buses may take a variety of forms, including electrically conductive paths such as wires or electrical cables, or optical paths such as fiber optical cable.

The transducer array 202 produces and transmits ultrasound into a body, tissue or other material. The transducer array 202 also receives ultrasound returns or echoes and produces analog transducer element voltage signals of analog return signal which are induced at the transducer array by the received ultrasound returns or echoes. The transducer array 202 may take the form of a solid state device that provides electronic control capabilities, variable aperture, excellent image performance and high reliability. The transducer array 202 may, for example, take the form of either a flat linear array or a curved linear array of elements. A curved linear array may provide a broad sector scanning field. The geometric curvature of a curved linear array may advantageously reduce steering delay requirements on a beamformer of the front end ASIC 206. Where the transducer array 202 takes the form of a flat array, the beamformer functionality of the front end ASIC 206 may be capable of producing sufficient delay to both steer and focus, for example operating the transducer elements of the transducer array 204 as a phased array.

The transmit/receive ASIC 204 is communicatively coupled to the transducer elements of the transducer array 202. The transmit/receive ASIC 204 drives the transducer elements. The transmit/receive ASIC 204 receives representations of ultrasound returns or in the form of analog transducer element voltage signals or analog return signals. The transmit/receive ASIC 204 implants an analog amplification stage, amplifying (i.e., analog amplification) the analog transducer element voltage signals. The analog amplification typically varies with imaging depth (i.e., time gain compensation or TGC) to compensate for attenuation of ultrasound with depth. The transmit/receive ASIC 20 also controls the active transmit and receive apertures of the transducer array 202 and the gain of the received analog return signals or echoes.

The transmit/receive ASIC 204 may be positioned proximate the transducer array 200, for example within inches of the elements of the transducer array 202 to ensure short communications path. The transmit/receive ASIC 204 may, for example, be positioned in the same enclosure and just behind the transducer array 202. U.S. Pat. No. 5,893,363 titled ULTRASONIC ARRAY TRANSDUCER TRANSCEIVER FOR A HANDHELD ULTRASONIC DIAGNOSTIC INSTRUMENT describes a suitable transmit/receive ASIC.

The front end ASIC 206 receives the analog return signals from the transmit/receive ASIC 204 in the form of amplified analog transducer element voltage signals. The front end ASIC 206 beamforms the analog return signals from the individual elements of the transducer array 202 into coherent scanline signals. For example, the front end ASIC 206 includes an analog-to-digital converter (ADC) or implements analog-to-digital conversion 212 for each channel (only one shown), forming an analog-to-digital conversion stage which digitizes the amplified analog transducer element voltage signals and produces digitized return signals. The front end ASIC 206 may also include delay circuitry or implements delay functionality 214 to apply delays to the digitized return signals. The front end ASIC 206 further includes summing circuitry or implements summing functionality 216, which sums the digitized return signals of the various channels.

The front end ASIC 206 also includes transmit and timing control circuitry or implements transmit and timing control functionality 218, providing control signals to the transmit/receive ASIC 204 to control transmit waveform timing, aperture and focusing of the ultrasound beam. In the illustrated embodiment, the front end ASIC 206 provides timing signals for the other ASICs and time gain control (TGC). For example, the front end ASIC 206 may include time gain control weighting factor circuitry or implement time gain control weighting factor functionality 220. The front end ASIC 206 may include digital-to-analog converter(s) or implement digital-to-analog conversion functionality 222. The front end ASIC 206 may be communicatively coupled to a computer- or processor-readable storage device such as a memory 224; which stores data used by the beamformer. U.S. Pat. No. 5,817,024 entitled HANDHELD ULTRASONIC DIAGNOSTIC INSTRUMENT WITH DIGITAL BEAMFORMER and U.S. Pat. No. 5,893,363 entitled ULTRASONIC ARRAY TRANSDUCER TRANSCEIVER FOR HAND HELD ULTRASONIC DIAGNOSTIC INSTRUMENT each describe suitable front end ASICS and operation.

In addition to the above described functionality, the front end ASIC 206 also advantageously includes ADC saturation monitor and response circuitry or provides ADC saturation monitor and response functionality 225 which monitors ADC saturation and responds by performing or causing performance of one or more actions. For example, the ADC saturation monitor and response circuitry or functionality 225 may control, prevent or reduce a frequency of occurrence of ADC saturation in the analog-to-digital conversion of the analog return signals of each channel as a function of depth (i.e., sample index). In particular, the ADC saturation monitor and response circuitry or functionality 225 may be configured as an analog-to-digital conversion feedback stage to monitor values that are indicative of a ADC saturation condition for each channel as a function of depth, and to adjust a gain in a depth dependent analog amplification in order to prevent such ADC saturation or reduce the occurrence of such ADC saturation. The ADC saturation monitor and response circuitry or functionality 225 may be further configured to provide an adjustment or compensation in a digital gain to compensation for the adjustment to the analog gain.

Also for example, the ADC saturation monitor and response circuitry or functionality 225 may additionally, or alternatively, provide one or more signals which cause an alert to be provided via a user interface of the ultrasound imaging system. Such may allow a user to manually adjust various operational parameters, for instance analog gain. As a further example, the ADC saturation monitor and response circuitry or functionality 225 may additionally, or alternatively, adjust a defined time gain compensation or control profile. As an even further example, the ADC saturation monitor and response circuitry or functionality 225 may additionally, or alternatively, adjust a power consumption state of at least a portion of the ultrasound imaging system. For instance, the ADC saturation monitor and response circuitry or functionality 225 may cause the ultrasound imaging system or some portion thereof to enter a low power consumption mode upon determining that no imaging is currently being performed based on an absence of significant ADC saturation, particular when employing a relatively low ADC saturation threshold.

The ADC saturation monitor and response circuitry or functionality 225 of the front end ASIC 206 may monitor the output (i.e., ADC values) of the ADC for each channel as a function of depth, updating one or more saturation status registers or counters. The ADC saturation monitor and response circuitry or functionality 225 may, from time-to-time, read saturation status information from one or more saturation status registers or counters to analyze an ADC saturation condition as a function of depth, possibly as a function of channel, and/or possibly as a function of other parameters such as ray index, focal zone, and/or mode (e.g., 2D echo; Doppler). The ADC saturation monitor and response circuitry or functionality 225 may adjust analog amplification or TGC based on such information to increase or enhance utilization of a dynamic range of the ADC(s) where possible, while avoiding saturation. Thus, analog gain may be reduced at depths where excessive saturation is encountered, met or exceeded. Analog gain may be increased where doing so will not cause excessive saturation. The ADC saturation monitor and response circuitry or functionality 225 should accomplish such control while preventing unnecessary oscillation. For instance, the ADC saturation monitor and response circuitry or functionality 225 may employ a feedback mechanism such as digital filter function to achieve stability. The ADC saturation monitor and response circuitry or functionality 225 may advantageously employ even more sophisticated approaches that rely on saturation information accumulated over time, for instance adaptive filters (e.g., data dependent).

Figure 2B:
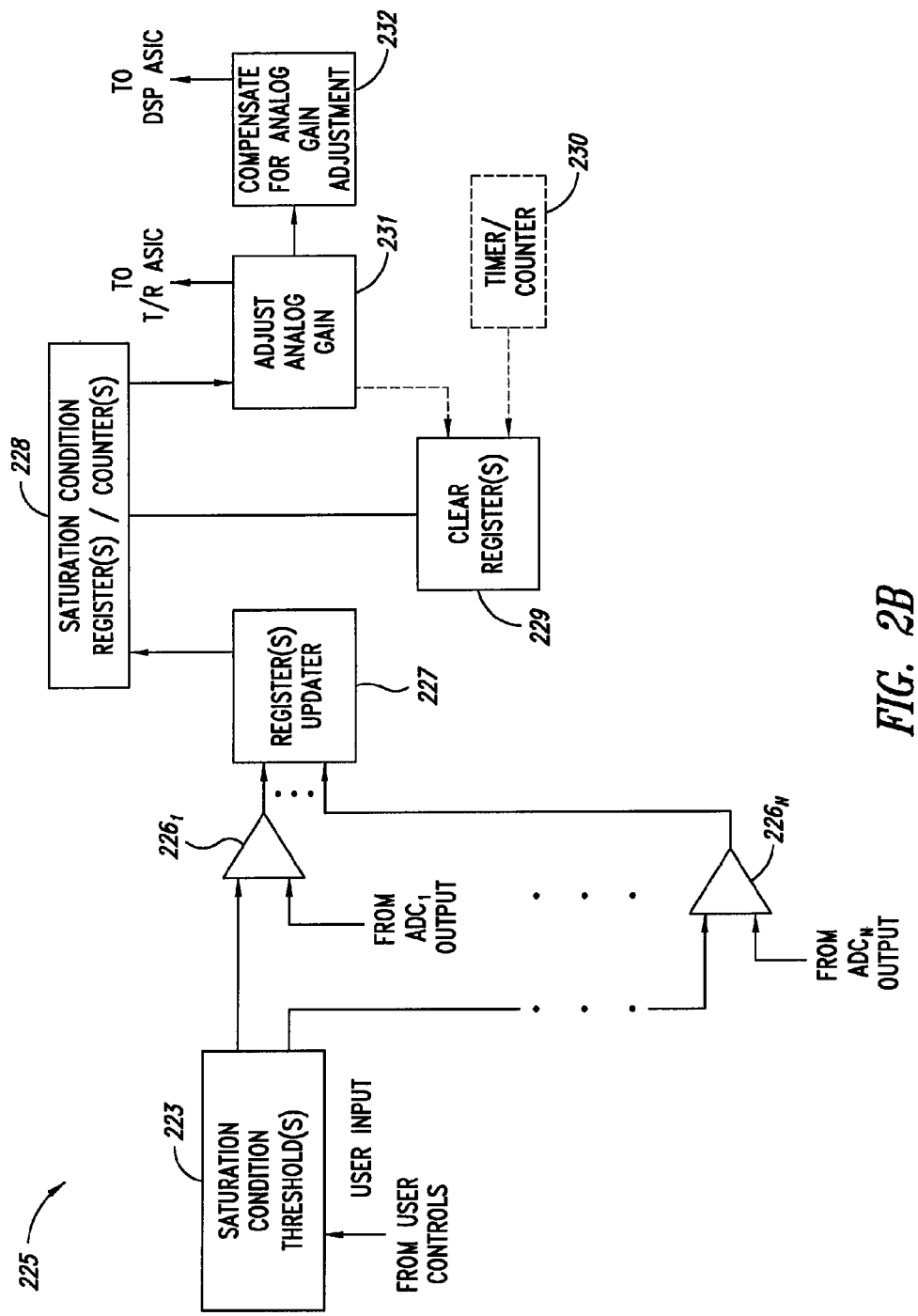
FIG. 2B is a schematic diagram of ADC saturation monitor circuitry or functionality of an ultrasound imaging system according to one illustrated embodiment.

As best illustrated in FIG. 2B, the ADC saturation monitor and response circuitry or functionality 225 includes one or more saturation condition detectors, which may take the form of one or more comparators or may implement a comparison functionality $226_1$-$226_N$ (collectively 226). The comparators or comparison functionality 226 may compare the output of respective ADCs or ADC values to one or more threshold values to determine whether an ADC saturation condition has been encountered, met or exceeded. The threshold value(s) may be stored in a computer- or processor-readable saturation condition threshold storage medium 223. Such threshold value(s) may be user configurable, for instance by user input received via the user controls. Alternatively, the threshold value(s) may be preset, for example by the manufacturer of the ultrasound imaging system. Default threshold value(s) may be defined. Threshold values may, for example, be logically associated with different operational modes.

The saturation condition detectors may detect a variety of events or conditions, based on the particular threshold values. For instance, the threshold values may be set such that the saturation condition detectors detect actual saturation of the respective ADCs. Alternatively, the threshold values may be set such that the saturation condition detectors detect an approach to an actual saturation of the respective ADCs. Alternatively, the threshold values may be set such that the saturation condition detectors detect non-saturation of the ADCs. For instance, the threshold may be set well below a value at which saturation of the ADCs occurs. Such may indicate that the analog amplification or gain is too low and should be adjusted upwards to increase or maximize use of the available dynamic range of the ADCs. Such may also indicate that imaging is not currently being performed, allowing the ultrasound imaging system or some portions thereof to enter into a power saving, low power consumption mode.

Multiple threshold values may be employed, for example a relatively higher set of values indicative of saturation actually occurring or about to occur, and a relatively lower set of values indicative of a lack of actual saturation and hence a failure to use the desired expanse of the dynamic range of the ADCs. Thus, analog amplification or gain may be increased in response to detection of values at or exceeding the relatively higher set of threshold values, and decreased in response to detection of values at or below the relatively lower set of threshold values. Such may advantageously enhance use of ADC dynamic range.

The ADC saturation monitor and response circuitry or functionality 225 may include a register(s) updater or implement registers(s) update function 227. The register(s) updater or registers(s) update function 227 updates one or more saturation condition registers or counters 228 to reflect the outcome of the comparisons. For example, the register(s) updater or update function 227 may set a respective bit of a saturation status register 228 if a saturation condition is encountered, met, exceeded or occurs at a respective range of depths for a respective channel. For instance, a saturation status register 228 with a set number of bits (e.g., 16 bits) may be used to represent a full range of depths for a given analog channel or ADC. Also for example, the register(s) updater or update function 227 may increment a respective counter 228 if a saturation condition is encountered, met, exceeded, or occurs at a respective range of depths for a respective channel. As a further example, the register(s) updater or update function 227 may increment a common channel counter 228 for a range of depths if a saturation condition is encountered, met, exceeded, or occurs at a respective range of depths for any of the channels. The denomination "common" as used in reference to a common channel counter means that the counter is common to or tracks the status for more than one channel.

The ADC saturation monitor and response circuitry or functionality 225 may include a register(s) clearer or implement a clear register(s) function 229. The register(s) clearer or clear register(s) function 229 may clear the saturation condition register(s) or counter(s) from time-to-time. Such may occur periodically, for example in response to a signal from a timer, clock or counter 230. Alternatively or additionally, such may occur non-periodically. For example, the register(s) clearer or clear register(s) function 229 may clear one or more saturation condition registers or counters in response to an occurrence of an event or condition. For instance, the register(s) clearer or clear register(s) function 229 may clear one or more saturation condition registers or counters in response to an adjustment of analog amplification of gain for the channel(s) and/or range of depths.

The ADC saturation monitor and response circuitry or functionality 225 may include an analog amplification or gain adjustor or implement an analog amplification or gain adjustor function 231. The analog amplification or gain adjustor or analog gain adjustor function 231 determines an amount of adjustment to be made to the analog amplification or gain for each channel as a function of depth. Such may be to prevent or reduce saturation of the respective ADC, and produces signals which cause the determined adjustments in the analog gain or amplification. For example, the analog amplification or gain adjustor or analog amplification or gain adjustor function 231 may determine an amount of adjustment that is sufficient to prevent or reduce the of occurrence of saturation of the ADC for each channel as a function of depth. The analog gain amplification or adjustor or analog amplification or gain adjustor function 231 may provide appropriate controls signals to the transmit/receive ASIC 204 to implement the determined adjustment. Such may also be used to increase saturation to some nominal level, which may ensure that the analog amplification or gain has not been adjusted too low. Such may also be used to determine an activity level of the ultrasound imaging system, allowing entry into an energy saving or a low power consumption state.

The ADC saturation monitor and response circuitry or functionality 225 may optionally include compensation circuitry or implement a compensation functionality 232 that causes an adjustment or compensation in a digital gain or amplification to compensate for the analog gain or amplification adjustments. For example, the compensation circuitry or compensation functionality 232 may determine an amount of adjustment or compensation to be made in the gain or amplification of the digital return signal to at least partially offset for the adjustment made in the amplification of the analog return signal. The compensation circuitry or compensation functionality 232 may provide one or more signals to the DSP ASIC 208 indicative of a determined adjustment or compensation to be made in the digital gain or amplification to compensate for the adjustment to the analog amplification.

Various approaches may be employed in implementing the ADC saturation control functionality. For example, a saturation status approach may be employed which tracks a saturation status (i.e., has a saturation condition occurred) for each of a number of ranges of depths for each channel. Also for example, a respective channel counter approach may be employed which tracks a total number of times a saturation condition has occurred for each of a number of ranges of depths for each channel. As a further example, a common channel counter approach may be employed which tracks a total number of times a saturation condition has occurred for each of a number of ranges of depths for any of the channels. These approaches are discussed in more detail below in reference to various methods of operating the ultrasound imaging system architecture 200.

Returning to FIG. 2A, the DSP ASIC 208 acts as a digital processor stage, receiving beamformed scanline signals from the front end ASIC 206 and processing the same. The DSP ASIC 208 filters the scanline signals, amplifies the scanline signals and processes the filtered scanline signals as B mode signals, Doppler signals, or both. For example, DSP ASIC 208 includes circuitry or implements one or more filters (not shown) and one or more amplifiers or implements an amplification functionality 233.

In some embodiments, the DSP ASIC 208 may provide several advanced features including synthetic aperture formation, frequency compounding, Doppler processing such as power Doppler (e.g., color flow or color power) processing, and speckle reduction as more fully detailed below. For example, the DSP ASIC 208 may include appropriate circuitry for or may implement a synthetic aperture functionality 234, a frequency compounding functionality 236, and/or Doppler processing functionality 238 to perform power Doppler processing. The DSP ASIC 208 may be communicatively coupled to a computer- or processor-readable storage device such as 3D CPA memory 240 to provide storage used in three dimensional power Doppler (3D CPA) imaging.

The back end ASIC 210 receives the ultrasound B mode and Doppler information from the DSP ASIC 208. The back end ASIC 210 implements a scan conversion 242 that performs scan conversion and produces video output signals or frames of video 244. The back end ASIC 210 may be configured to add alphanumeric information to the display such as the time and/or date via a time and/or date function 246, and patient identification. A graphics processor 248 may overlay the ultrasound images with information such as depth and focus markers and cursors. Frames of ultrasonic images 244 may be stored in a video memory 250 communicatively coupled to the back end ASIC 210. Such may allow selected frames to be recalled and replayed, for instance in a live Cineloop® real-time sequence. Video information may be available at a video output. The video information may be made available in a variety of formats, for instance NTSC and PAL formats or RGB drive signals for an integral display 252 or other a video monitor.

The back end ASIC 210 includes a central processor 254, for example a reduced instruction set controller (RISC) or other microprocessor or controller. The central processor 254 may execute instructions and/or program data stored on one or more computer- or processor-readable storage devices, for example a program memory 256.

The central processor 254 is communicatively coupled to the front end ASIC 206 and DSP ASIC 210 to control and synchronize the processing and control functions throughout the ultrasound imaging system architecture 200. For example, the central processor 254 may coordinate process timing and loading of buffers and registers with the data necessary to perform the processing and display requested by the user. Timing for the central processor 254 is provided by clock signals from the clock generator, which may be located on or implemented by the front end ASIC 206.

The central processor 254 is operated under user control by commands, selections and/or entries made by the user via the user controls 260. As described above, the user controls 260 allow a user to direct and control the operations of the ultrasound imaging system architecture 200. Where a handheld form factor is employed, a number of functions, such as patient data entry, Cineloop® operation, and 3D review, may be operated through menu control provided via a graphical user interface. Such may advantageously minimize the number of keys, buttons or switches present on a small handheld housing. Additionally, or alternatively, a number of operational functions may be programmed to be logically associated with specific diagnostic applications. Such operational functions may be automatically executed or performed when a specific operating mode or application is selected by a user. For example, selection of B mode imaging may automatically invoke frequency compounding and depth dependent filtering on the DSP ASIC 208, while selection of Doppler operation may cause automatic set up of a four multiplier filter as a wall filter on the DSP ASIC 208. The menu selection of specific clinical applications can, for example, automatically invoke specific feature settings such as TGC control characteristics and focal zones.

The central processor 254 may be communicatively coupled to a communications port (e.g., Universal Serial Bus or USB port, Ethernet port, FIREWIRE® port, infrared transmitter/receiver) 258. The communications port 258 allows other modules and functions to be communicatively coupled to or communicate with the ultrasound device. The communications port 258 can communicatively couple to a modem or communications link to transmit and receive ultrasound images, ultrasound information and/or other information from remote locations. The communications port 258 can accept other data storage devices to add new functionality to the ultrasound device, for instance an ultrasound information analysis package. The communications port 258 may also allow the processor 254 to access additional program instructions or data and/or transmit image information remotely.

A power and battery management subsystem 262 applies battery power to the other components and subsystems of the ultrasound imaging system. For example, the power and battery management subsystem 262 may monitor and control electrical power applied to the transducer array 202, thereby controlling the acoustic energy which is applied to the patient. The power subsystem 262 may also be configured to minimize overall power consumption of the ultrasound imaging system. The power subsystem 262 may provide electrical power from a portable power storage device (e.g., rechargeable battery cells, ultra-capacitor array, fuel cell array), particularly where the ultrasound imaging system takes the form of a handheld or portable device. The power subsystem 262 may include a DC-DC converter to convert the low battery voltage to a higher voltage which is applied to the transmit/receive ASIC 204 to drive the elements of the transducer array 202. The power subsystem 262 may include a rectifier and step down converter to convert AC power to recharge the power storage device (e.g., rechargeable battery cells, ultra-capacitor array).

While the various components are generally described above as being housed in a single unitary or single piece housing, other alternatives will be readily apparent from this description. For instance, the front end ASIC 206, the DSP ASIC 208, and the back end ASIC 210 could be located in a common enclosure, with the beamformer of the front end ASIC 206 physically and/or communicatively detachably coupled to the elements of the transducer array 202. This allows different transducer arrays to be used with the digital beamformer, digital filter, and image processor for various diagnostic imaging procedures. The display 252 could be located in the same enclosure as the front end, DSP and back end ASICs, or the output of the back end ASIC 210 could be connected to a separate display device. Alternatively, the transducer array 202, transmit/receive ASIC 204 and front end ASIC 206 could be housed in a transducer housing, with the DSP ASIC 208, back end ASPIC 210, user controls 260 and display 252 housed in a separate housing. Other variations are possible.

Figure 3:
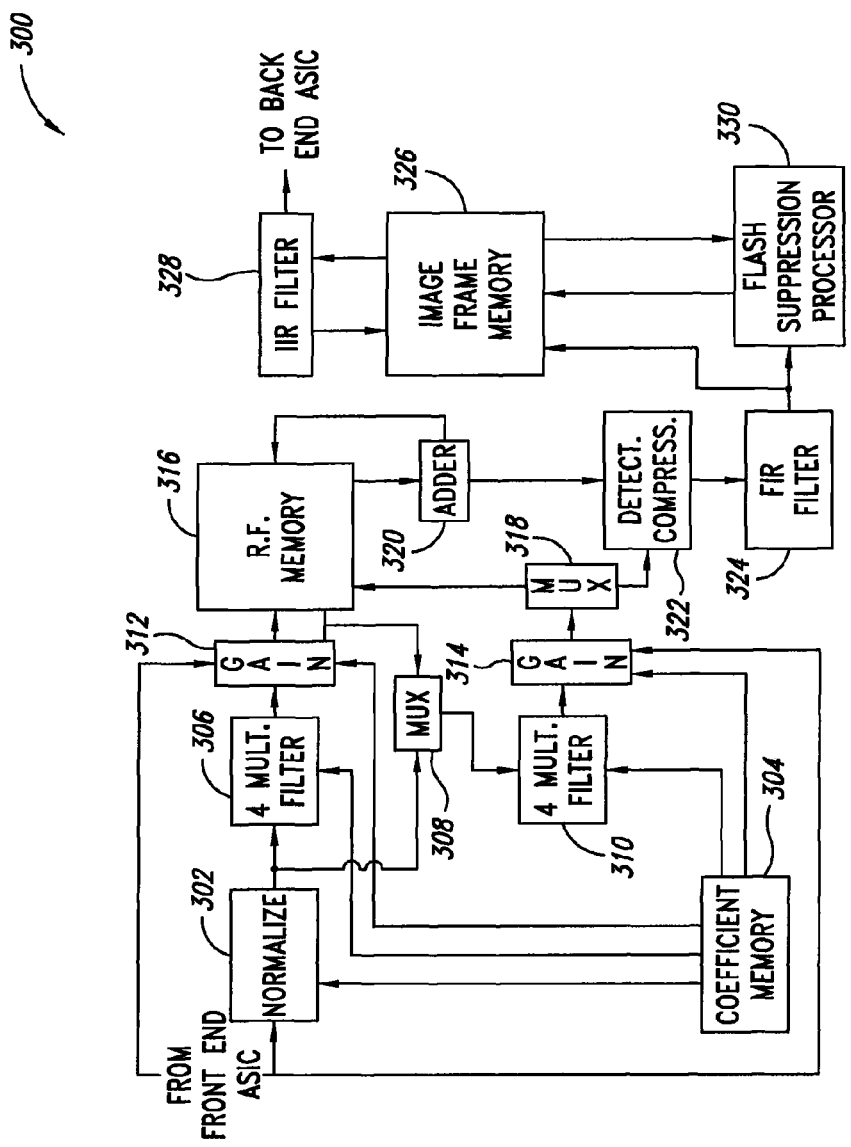
FIG. 3 is a schematic diagram of the digital signal processing ASIC of the system architecture of FIG. 2A according to one illustrated embodiment.

FIG. 3 shows a DSP ASIC 300 according to one illustrated embodiment. The DSP ASIC 300 may be used to implement the DSP ASIC 208 (FIG. 2A).

The DSP ASIC 300 includes normalization circuitry or implements a normalization functionality 302 which receives scanline signals from a front end ASIC, for example front end ASIC 206 (FIG. 2A). The normalization circuitry or functionality 302 multiplies the received scanline signals by a variable coefficient stored in a coefficient memory 304 to normalize the received signals for aperture variation.

The ultrasound imaging system may be operated in the B mode to form a structural image of tissue and organs or may be operated to process Doppler echo signals for power Doppler (CPA) display The DSP ASIC 300 may include a first four multiplier filter 306, a multiplexer 308, and a second four multiplier filter 310. Each of the four multiplier filters 306, 310 includes a multiplier and an accumulator which operate as a finite impulse response (FIR) filter. The four multiplier filters 306, 310 may perform decimation band pass filtering, and may reduce radio frequency (R.F.) noise and quantization noise through bandwidth limiting effects. I and Q return or echo signal samples are produced at the outputs of filters 306 and 310, amplified if desired by the multipliers of gain stages 312, 314, then stored in the R.F. memory 316. The Q samples are coupled to the R.F. memory 316 by a multiplexer 318.

A compression circuit 322 includes two shift registers and a multiplier arranged to form a CORDIC processor for performing envelope detection. The detected signal is compressed and scaled to map the detected signals to a desired range of display gray levels.

A FIR filter 324 may perform low pass filtering of the grayscale signals. If the selected scanning mode utilizes a single transmit focal point, the grayscale signals are transmitted to the back end ASIC 210 (FIG. 2A) for scan conversion. Prior to leaving the DSP ASIC 300, the grayscale signals can be frame averaged by an infinite impulse response (IIR) filter 328 which utilizes image frame memory 326 as a frame buffer and incorporates one multiplier and two adders to perform frame to frame averaging.

The user may choose to process the grayscale image with certain image enhancement features, such as depth dependent filtering or speckle reduction such as the frequency compounding technique described in U.S. Pat. No. 4,561,019.

The DSP ASIC 300 may also include a flash suppression processor 330 which may operate by any of a number of known flash suppression techniques, such as frame to frame comparison and elimination or the notch filtering technique of U.S. Pat. No. 5,197,477. One suitable technique for flash suppression processing is min-max filtering as described in detail in the parent, U.S. Pat. No. 5,722,412.

Figure 6:
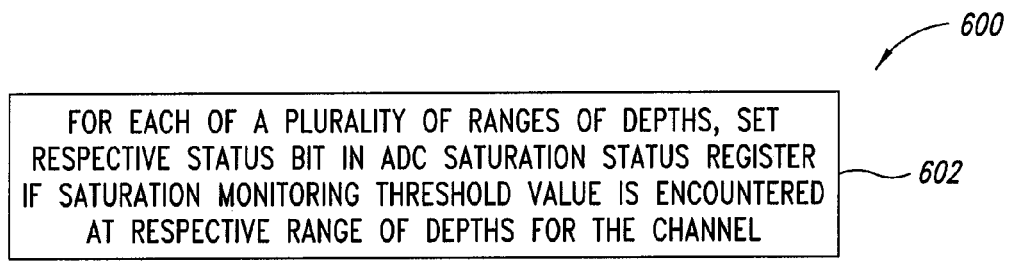
FIG. 6 is a low level flow diagram of a method of monitoring an ADC value for each channel as a function of depth using a status bit register according to one illustrated embodiment.
Figure 7:
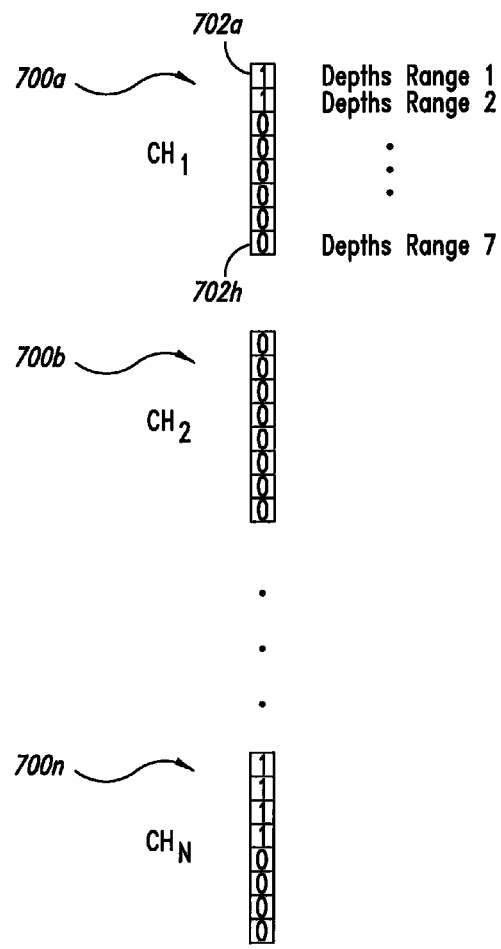
FIG. 7 is a schematic diagram of a set of saturation status registers according to one illustrated embodiment, each saturation status register having a number of bits corresponding to respective ones of a number of ranges of depths.

The sequences of operating the DSP ASIC 300 for B mode (two dimensional) echo and Doppler processing, respectively, are described in more detail in flowcharts of FIGS. 6 and 7, respectively, of U.S. Pat. No. 7,604,596.

The image frame memory 326 and its associated flash suppression processor 330 and IIR filter 328 can be located on the back end ASIC 210 (FIG. 2A), thereby partitioning the DSP ASIC 300 and the back end ASIC 210 (FIG. 2A) at the output of FIR filter 324. Thus, the digital signal processing function of FIG. 3 up through the output of FIR filter 324, or all of the functions shown in FIG. 3 can be fabricated on a single integrated circuit chip, depending upon this partitioning choice and other integrated circuit layout considerations.

Figure 4:
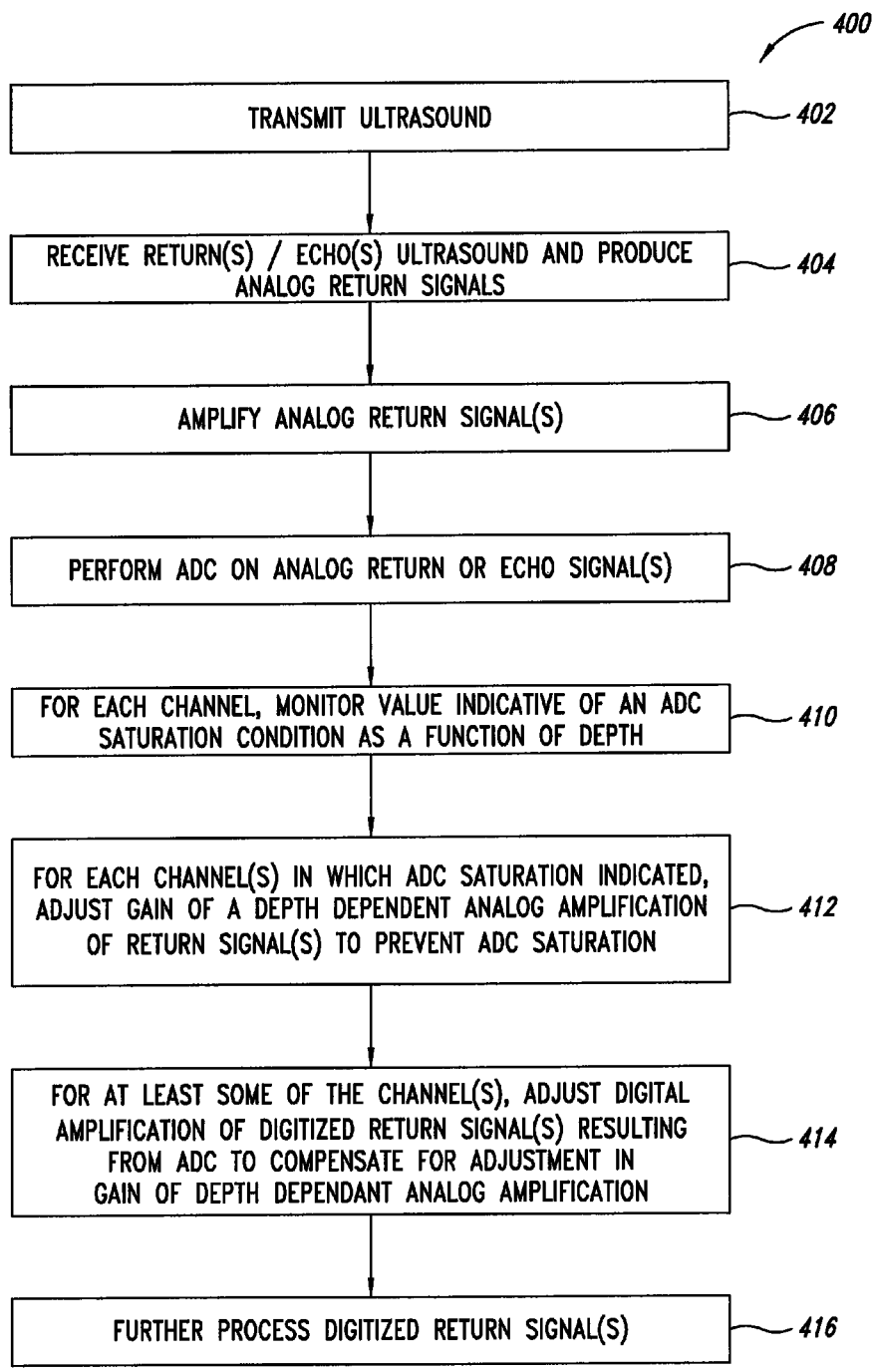
FIG. 4 is a high level flow diagram of a method of operating an ultrasound imaging system according to one illustrated embodiment.

FIG. 4 shows a high level method 400 of operating an ultrasound imaging system, according to one illustrated embodiment. The method 400 focuses on aspects of the operation related to ADC saturation control, and in the interest of clarity and brevity omits many general details of operation that are set out in other descriptions of ultrasound imaging system, for instance U.S. Pat. No. 7,604,596. The method 400 is discussed with reference to FIGS. 2A and 2B.

At 402, the ultrasound imaging system transmits ultrasound into a medium, for example into bodily tissue. In particular, the transmit/receive ASIC 204 (FIG. 2A) may cause the transducer elements of the transducer array 202 to transmit ultrasound in response to control by the front end ASIC 206, DSP ASIC 208 and the central processor 254 of the back end ASIC 210. Also as previously explained, for example operating the transducer elements as a phased array.

At 404, the ultrasound imaging system receives return or echo ultrasound. In particular, the transducer elements of the transducer array 202 (FIG. 2A) may receive returned or echo ultrasound from the body, tissue or other material. The transducer elements transform such into analog return signals, which may be electrical signals having a voltages corresponding to a magnitude of the return or echo ultrasound. The transducer array 202 (FIG. 2A) may provide the analog return signals to the transmit/receive ASIC 204.

At 406, the ultrasound imaging system amplifies the analog return signals. In particular, the transmit/receive ASIC 204 (FIG. 2A) may amplify the analog return signals received from the transducer elements of the transducer array 202. As described herein, a gain in amplification of the analog signals may be adjusted to control ADC saturation.

At 408, the ultrasound imaging system performs analog-to-digital conversion on the analog return signals. In particular, for each channel a respective ADC 212 (FIG. 2A) of the front end ASIC 206 converts the analog return signals to digitized or sampled return signals. As previously explained, analog-to-digital conversion may result in clipping if saturation is not adequately controlled.

At 410, for each channel, the ultrasound imaging system monitors a value that indicative of an ADC saturation condition as a function of depth. For example, a comparator or comparison function 226 of the front end ASIC 206 may monitor for the occurrence of an ADC saturation condition as a function of depth. In particular, the comparator or comparison function $226_1$-$226_N$ (FIG. 2B) of the front end ASIC 206 (FIG. 2A) may compare a value with a saturation condition threshold, determining when the saturation condition threshold is encountered, met or exceeded. The comparison may include comparing to both a maximum positive saturation condition threshold and a maximum negative saturation condition threshold. The saturation condition threshold may be set such that encountering, meeting or exceeding the saturation condition threshold is indicative of saturation actually occurring. Alternatively, the saturation condition threshold may be set such that encountering, meeting or exceeding the threshold is indicative of approaching or being within some amount or percentage of saturation occurring. The results of the comparison may be saved, for example to a saturation condition register or counter. For instance, if a saturation condition is encountered, met or exceeded, a status bit may be set or a counter may be incremented. The monitoring 410 may be continuous or periodic during the operation of the ultrasound imaging system, or may be non-periodic. While illustrated as monitoring values downstream or after analog-to-digital conversion, some embodiments may monitor values upstream of or before the analog-to-digital conversion. For example, the ultrasound imaging system may monitor a magnitude of a voltage of the analog return signals provided from the transmit/receive ASIC 204 before digitization or sampling by the ADCs.

At 412, for at least one of the channels of the ultrasound imaging system, adjusts a gain of a depth dependent analog amplification of at least one analog return signal produced by at least one transducer element based at least in part on the monitoring to prevent saturation in the analog-to-digital conversion of the at least one analog return signal. In particular, an analog gain adjustor or analog gain adjustor functionality 231 (FIG. 2B) of the front end ASIC 206 (FIG. 2A) may determine an amount of adjustment, and may provide a corresponding signal to the transmit/receive ASIC 204 to adjust the gain or amplification of the analog return signals. The adjustment may, for example, be linear or may be non-linear. The adjustment may ensure that clipping does not occur, or may only reduce the probability or frequency of clipping occurring. The analog gain adjustor or analog gain adjustor function 231 may employ one or more saturation condition registers or counters 231 FIG. 2B) to determine which channels to adjust, and to determine the amount or level of adjustment. The registers or counters 231 may, for example, be cleared or reset after adjustment. The adjusting 412 may be continuous or periodic, or may occur non-periodically. The adjusting 412 may run or be executed in parallel with the monitoring 410, for example as separate threads in a multi-threaded process.

Optionally at 414, for at least some of the channels, the ultrasound imaging system adjusts a digital amplification of a digital return signal resulting from an analog-to-digital conversion of the at least one analog return signal to compensate for the adjusting of the gain of the depth dependent analog amplification. In particular, a compensation circuitry or compensation functionality 232 (FIG. 2B) of the front end ASIC 206 (FIG. 2A) may determine an amount of adjustment and provide a corresponding signal to the DSP ASIC 208 to adjust the gain produced by amplification of the digitized return signals. The adjustment or compensation may, for example be linear, or may be non-linear. The adjustment or compensation may completely or fully compensate for the adjustment in the analog amplification or gain, or may only partially compensate for the adjustment in the analog amplification or gain.

Optionally at 414, the ultrasound imaging system further processes the digitized return signals. For example, the DSP ASIC 208 may sum the digital return signals of a plurality of channels. Such summing may occur downstream of the monitoring of the analog-to-digital conversion value resulting from the analog-to-digital conversion for the channel as a function of depth.

Figure 5:
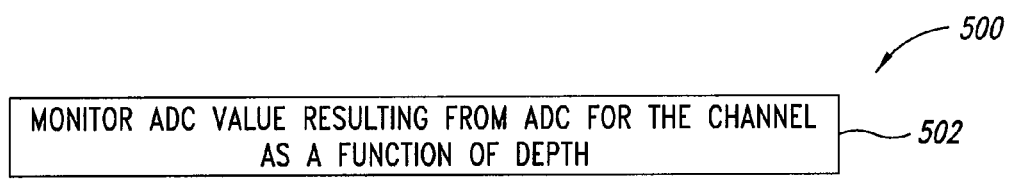
FIG. 5 is a low level flow diagram of a method of monitoring a value indicative of an ADC saturation condition according to one illustrated embodiment.

FIG. 5 shows a method 500 of monitoring a value indicative of an ADC saturation condition according to one illustrated embodiment. The method 500 may be useful in performing the monitoring of values indicative an ADC saturation condition 410 of the method 400 (FIG. 4).

At 502, the ultrasound imaging system monitors ADC values resulting from analog-to-digital conversion for a channel as a function of depth. In particular, the front end ASIC 206 may monitor the magnitude of digitized return signals from respective ones of the ADCs 212 (FIG. 2A). As described herein, monitoring may include comparing a magnitude of the digitized return signals to a saturation condition threshold.

FIG. 6 shows a method 600 of monitoring an ADC value for each channel as a function of depth using a status bit register according to one illustrated embodiment. The method 600 may be useful in performing the monitoring of ADC values for each channel as a function of depth 502 of the method 500 (FIG. 5).

At 602, for each of a plurality of ranges of depths, the ultrasound imaging system sets a respective status bit in ADC saturation status register if saturation monitoring threshold value is encountered, met or exceeded at the respective range of depths for the channel. The saturation status registers may be cleared from time-to-time, for instance periodically or non-periodically, for instance in response to the occurrence of an event. For example, a saturation status register may have all bits cleared (e.g., 0). Then selected bits in the register corresponding to certain ranges of depths are set (e.g., 1) if a saturation condition is encountered, met or exceeded at the respective range of depth. Later the bits of the register may again be cleared.

FIG. 7 shows a set of saturation status registers 700a-700n (collectively 700) according to one illustrated embodiment. The saturation status registers 700 may be employed with a saturation status approach to implementing ADC saturation control, for instance the method 600 (FIG. 6).

The ultrasound imaging system may, for example, employ a respective saturation status register 700a-700n for each channel. Each register 700a-700n may have a number of bits 702a-702h (collectively 702, only two called out for one saturation status register in FIG. 7), each bit 702 assigned to carry a saturation status (e.g., Boolean values 0, 1) that indicates a saturation condition of a respective one of each of a number of respective ranges of depths for the channel. Thus, for example, for any given channel, any ranges of depths in which the saturation condition was encountered, met or exceeded may have a value 1 stored in the corresponding bit of the corresponding one of the saturation status registers 700. Other bits may have a value 0 stored therein, indicating that the saturation condition was not encountered, met or exceeded at the corresponding ranges of depths.

FIG. 8 shows analog gain as a function of depth for an exemplary operation of an ultrasound imaging system employing 1) a saturation status based approach to controlling ADC saturation; and 2) without controlling ADC saturation.

In particular, a first curve 900 shows the analog TGC as a function of depth without control of the ADC saturation. A second curve 902 shows analog TGC gain as a function of depth while controlling ADC saturation using a saturation status based approach, such as that of the method 600 (FIG. 6).

FIG. 9 shows a method 900 of monitoring an ADC value for each channel as a function of depth using a respective channel counter register for each channel according to one illustrated embodiment. The method 900 may be useful in performing the monitoring of ADC values for each channel as a function of depth 502 of the method 500 (FIG. 5).

At 902, for each channel and for each of a plurality of ranges of depths for that channel, the ultrasound imaging system increments a respective counter for the range of depths for the respective channel each time a saturation monitoring threshold is encountered, met or exceeded at the respective range of depths for the channel. In particular, the register(s) updater or update functionality 227 (FIG. 2B) may increment a counter for each range of depths for each channel each time a saturation condition is encountered, met or exceeded on that channel for that respective range of depth. The counters may be reset from time-to-time, for example periodically or in response to an occurrence of an event. The event may, for instance, be the adjustment of the analog amplification or gain, or some other event.

Figures 10, 11:
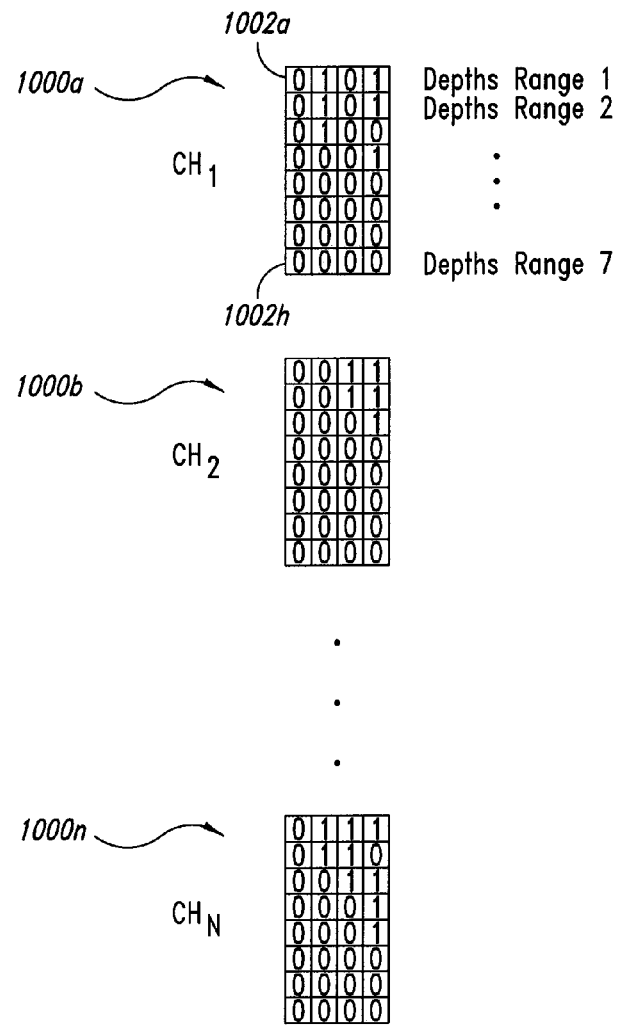
FIG. 10 is a schematic diagram of a set of respective channel counter registers according to one illustrated embodiment, each channel counter register having a number of sets of bits corresponding to respective ones of a number of ranges of depths to track a count for ranges of depths for the respective channel.
FIG. 11 is a low level flow diagram of a method of according to one illustrated embodiment.

FIG. 10 shows a set of counters in the form of respective channel counter registers 1000a-1000n (collectively 1000) according to one illustrated embodiment. The respective channel counter registers 1000 may be employed with a respective channel counter approach to implementing ADC saturation control, for instance the method 900 (FIG. 9).

The ultrasound imaging system may, for example, employ respective registers 1000a-1000n, one for each channel. Each register 1000a-1000n may have a number of sets of bits 1002-1002n (collectively 1002, only two called out for one register in FIG. 10), each set of bits 1002 assigned to carry a count that indicates a total number of times that a saturation condition has been encountered, met or exceeded for a respective one of each of a number of respective ranges of depths for the channel since the counter was last reset. Thus, for example, for any given channel, any ranges of depths in which a saturation condition has not been encountered, met or exceeded may store or contain a value 0 in the respective set of bits. Any ranges of depths in which a saturation condition has been encountered, met or exceeded once may store a value 1, encountered, met or exceeded twice may store a value 2, and so on as limited by the size of the register or counter. The channel counter register may be reset from time-to-time, for example periodically or in response to an occurrence of an event. The event may, for instance, be the adjustment of the analog amplification or gain, or some other event. A flag or other mechanism may be employed to monitor any occurrences of exceeding a limit (e.g., overflow) of the respective channel counter.

FIG. 11 shows a method 1100 of monitoring an ADC value for each channel as a function of depth using a common channel counter register which is common to each channel according to one illustrated embodiment. The method 1100 may be useful in performing the monitoring of ADC values for each channel as a function of depth 502 of the method 500 (FIG. 5).

At 1102, the ultrasound imaging system increments a count in the common channel counter register for the respective range of depth each time saturation monitoring threshold is encountered, met or exceeded at the respective range of depths for any of the channels. In particular, the register(s) updater or update functionality 227 (FIG. 2B) may increment a counter for each range of depths each time a saturation condition is encountered, met or exceeded on any one of the channels for that respective range of depth. The common channel counter register may be reset from time-to-time, for example periodically or in response to an occurrence of an event. The event may, for instance, be the adjustment of the analog amplification or gain, or some other event.

Figure 12:
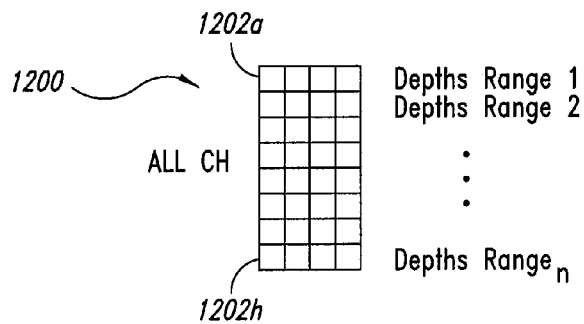
FIG. 12 is a schematic diagram of a common channel counter register according to one illustrated embodiment, the common channel counter register having a number of sets of bits corresponding to respective ones of a number of ranges of depths to track a count of a number of occurrences of saturation for all ADCs.

FIG. 12 shows a common channel counter in the form of a common channel counter register 1200, according to one illustrated embodiment. The common channel counter register 1200 may be employed with a respective common channel counter approach to implementing ADC saturation control, for instance the method 1100 (FIG. 11).

The common channel counter register 1200 may include a number of sets of bits 1202a-1202n, each set of bits 1202 assigned to carry a count that indicates a total number of times that a saturation condition has been encountered, met or exceeded for a respective one of each of a number of ranges of depths for any of the channels. Thus, for example, any ranges of depths in which a saturation condition has not been encountered, met or exceeded for any channel may store a value 0 in the respective set of bits. Any ranges of depths in which a saturation condition has been encountered, met or exceeded once for any of the channels may store a value 1, encountered, met or exceeded twice for any of the channels may store a value 2, and so on as limited by the size of the common channel counter register or other counter. A flag or other mechanism may be employed to monitor any occurrences of exceeding a limit (e.g., overflow) of the common channel counter.

Figure 13:
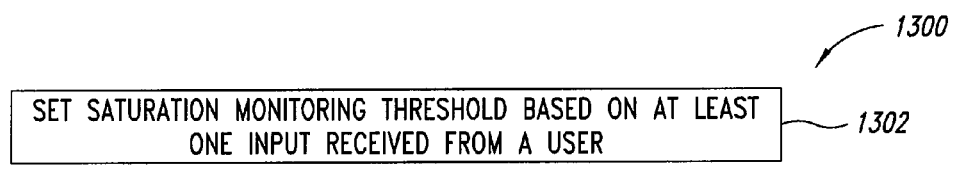
FIG. 13 is a low level flow diagram of a method of adjusting an ADC saturation condition according to one illustrated embodiment.

FIG. 13 shows a method 1300 of adjusting an ADC saturation condition, according to one illustrated embodiment. The method 1300 may, for example, be employed as an additional act in performing the method 400 (FIG. 4).

At 1302, the ultrasound imaging system sets a saturation monitoring threshold based at least on one input received from a user. For example, user input may be received by the central processor 254 (FIG. 2A) via the user controls 260. The central processor 254 may provide appropriate signals to the front end ASIC 206 to set the saturation monitoring threshold. For example, the signals may specify a positive and/or a negative saturation condition threshold value. The ultrasound imaging system may additionally, or alternatively, employ a default saturation monitoring threshold, for instance a maximum positive and/or maximum negative value for the ADC.

Figure 14:
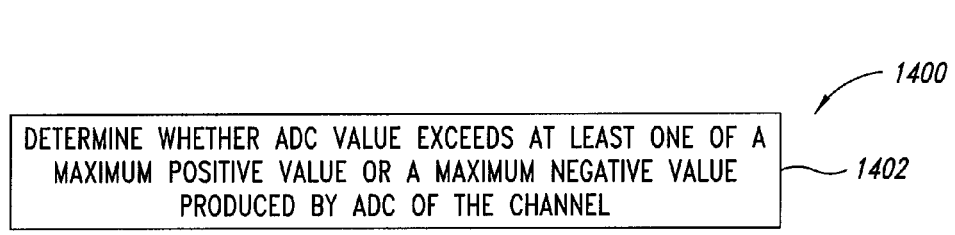
FIG. 14 is a low level flow diagram of a method of monitoring an ADC value according to one illustrated embodiment.

FIG. 14 shows a method 1400 of monitoring an ADC value, according to one illustrated embodiment. The method 1400 may be employed in performing the monitoring of ADC values for a channel as a function of depth 502 of the method 500 (FIG. 5).

At 1402, the ultrasound imaging system determines whether an ADC value produced by an ADC of a channel exceeds at least one of a maximum positive value or a maximum negative value. The maximum positive and/or maximum negative values may, for example, be predefined by a manufacturer of the ultrasound imaging system. The maximum positive and/or maximum negative values may be default values which are changeable by a user. Alternatively, maximum positive and/or maximum negative values may be fixed values.

Figure 15:
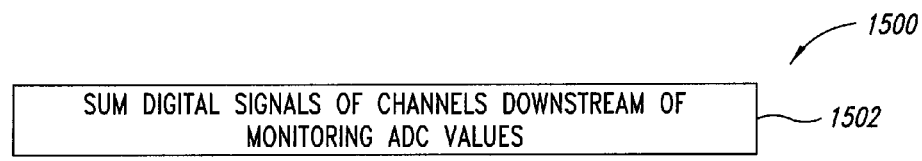
FIG. 15 is a low level flow diagram of a method of processing digitized return or echo signals according to one illustrated embodiment.

FIG. 15 shows a method 1500 of processing digitized return signals, according to one illustrated embodiment. The method 1500 may be employed in performing the further processing of digitized return signals 416 of the method 400 (FIG. 4).

At 1502, the ultrasound imaging system sums the digitized return signals of a plurality of channels. The summation is performed downstream of the monitoring of the ADC channels. In particular, the summer or summing function 216 (FIG. 2A) of the front end ASIC 206 may sum the digitized return signals of the various channels. Notably, monitoring of ADC saturation conditions upstream of the summing permits saturation conditions occurring on individual channels to be detected before such channel specific information is lost in the summing of the digitized return signals from various channels.

Figure 16:
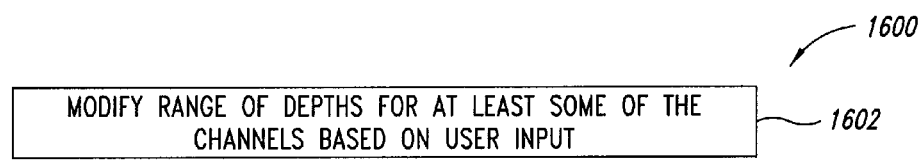
FIG. 16 is a low level flow diagram of a method of adjusting range of depths according to one illustrated embodiment.

FIG. 16 shows a method 1600 of adjusting range of depths, according to one illustrated embodiment. The method 1600 may be employed as an additional act in performing the method 400 (FIG. 4).

At 1602, the ultrasound imaging system modifies a range of depths for at least some of the channels. The modification may be in response to one or more user inputs. For example, user input may be received by the central processor 254 (FIG. 2A) via the user controls 260. The central processor 254 may provide appropriate signals to the front end ASIC 206 to set the range of depths. For example, the signals may specify a new range of depths. The ultrasound imaging system may additionally, or alternatively employ a default set of ranges of depths.

Figure 17:
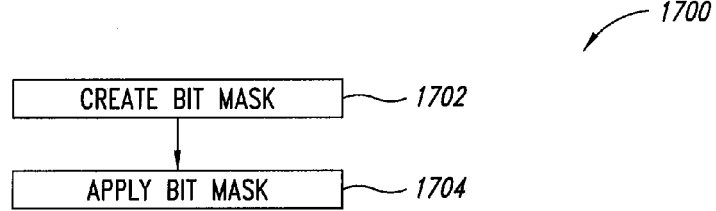
FIG. 17 is a low level flow diagram of a method of operating an ultrasound imaging system employing bitmasks according to one illustrated embodiment.

FIG. 17 shows a method 1700 of operating an ultrasound imaging system employing bitmasks according to one illustrated embodiment. The method 1700 may be employed as an additional act in performing the method 400 (FIG. 4).

The ultrasound imaging system may provide the ability to control the ADC saturation control functionality. For example, the ultrasound imaging system may provide a user with the ability to 1) enable or start, 2) disable or stop, and/or 3) clear or reset the ADC saturation control functionality. In particular, the ultrasound imaging system may allow these operations to be performed using a bit mask so that active depth-bits can be varied by transmit focal zones.

At 1702, the ultrasound imaging system creates a bit mask. At 1704, the ultrasound imaging system applies the bit mask to selectively mask off portions of ADC saturation status register corresponding to respective ones of a number of transmit focal zones.

For example, a bit mask 11110000 may be created, which during a zone 1 acquisition is applied to enable bits corresponding to a first transmit focal zone while disabling bits corresponding to a second transmit focal zone. Alternatively, a bit mask 00001111 may be created, which is applied during zone 2 acquisition to disable bits corresponding to a first transmit focal zone while enabling bits corresponding to a second transmit focal zone.

Figure 18:
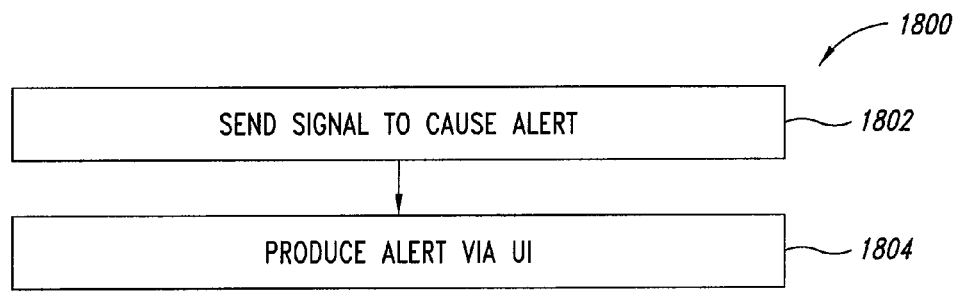
FIG. 18 is a low level flow diagram of a method of operating an ultrasound imaging system including producing an alert according to one illustrated embodiment.

FIG. 18 shows a method 1800 of operating an ultrasound imaging system according to one illustrated embodiment. The method 1800 may be used as part of, or in addition to the method 400 (FIG. 4), for instance being executed or performed in response to monitoring of values 410.

At 1802, the monitoring and response circuitry or functionality may send a signal to cause an alert. For example, the monitoring and response circuitry or functionality may send a sign to the central processor to cause one or more components of the user interface to produce an alert (e.g., visual, aural and/or tactile).

At 1804, one or more components of the user interface (e.g., display, speaker, vibrator) produces an alert. The alert may allow a user to manual change one or more of the operational settings of the ultrasound imaging system, for instance the analog amplification or gain, or some other operation setting for instance the mode.

Figure 19:
FIG. 19 is a low level flow diagram of a method of operating an ultrasound imaging system including adjusting a time gain compensation or control profile according to one illustrated embodiment.

FIG. 19 shows a method 1900 of operating an ultrasound imaging system according to one illustrated embodiment. The method 1900 may be used as part of, or in addition to the method 400 (FIG. 4), for instance being executed or performed in response to monitoring of values 410.

At 1902, the monitoring and response circuitry or functionality may adjust a time gain compensation or control profile. Such may be adjusted based on the magnitude and/or frequency of detected values exceeding the thresholds. The time gain compensation or control profile may be adjusted upwards, as well as downwards, depending on a desired result.

Figure 20:
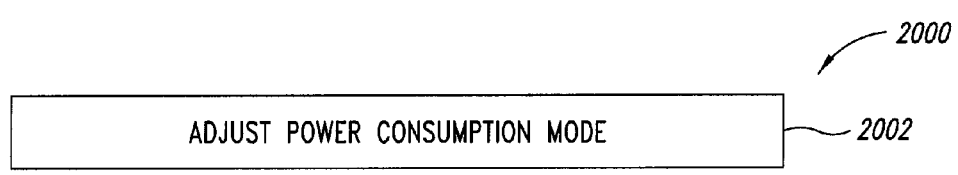
FIG. 20 is a low level flow diagram of a method of operating an ultrasound imaging system including adjusting a power consumption of the ultrasound imaging system or portions thereof according to one illustrated embodiment.

FIG. 20 shows a method 2000 of operating an ultrasound imaging system according to one illustrated embodiment. The method 2000 may be used as part of, or in addition to the method 400 (FIG. 4), for instance being executed or performed in response to monitoring of values 410.

At 2002, the monitoring and response circuitry or functionality may adjust a power consumption of the ultrasound imaging system or one or more portions thereof. For example, the monitoring and response circuitry or functionality may cause the ultrasound imaging system or one or more components thereof to enter a power savings or low power mode. Such may be in response to determining that there is a lack of saturation occurring, indicating that no imaging is currently occurring. A relatively low threshold condition may be set to detect such a condition. Additionally, or alternatively, the monitoring and response circuitry or functionality may cause the ultrasound imaging system or one or more components thereof to enter a normal operation or regular or high power mode. Such may be in response to determining that there is some nominal level of saturation occurring, indicating that imaging is currently occurring. The nominal level may be below some upper level at which saturation occurs too frequently but which may also be above some lower level at which sufficient use of the dynamic gain of the ADCs is not occurring. Such may advantageously allows power conservation while still increasing the use of the dynamic range of the ADCs.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other ultrasound systems, not necessarily the exemplary ultrasound imaging system generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors), as one of more field programmable gate arrays (FPGAs), as other firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any physical computer-readable medium for use by or in connection with any processor-related system or method. In the context of this disclosure, a memory is a computer-readable medium that is an electronic, magnetic, optical, or other physical device or means that contains or stores a computer and/or processor program. Logic and/or the information can be embodied in any computer-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "computer-readable medium" can be any physical element that can store the program associated with logic and/or information for use by or in connection with the instruction execution system, apparatus, and/or device. The computer-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Pat. No. 5,893,363 and U.S. Pat. No. 7,604,596 are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of operating an ultrasound imaging system, the method comprising:
    generating analog return signals in response to echo signals received from a number of depth ranges by a plurality of individual elements of a transducer that feed a plurality of channels of the ultrasound imaging system;
    converting the analog return signals in each channel to digital values with an analog to digital converter;
    monitoring the digital values in a number of depth range, each of which is smaller than an entire depth range from which echo signals are received in each of the channels with at least one component of the ultrasound imaging system to determine if a digital value of a return signal in a channel that is associated with an individual depth range is saturated; and
    adjusting a gain of the channel for the individual depth range associated with the digital value of the return signal that is saturated to reduce the saturation of the digital return signal in the channel.

2. The method of claim 1, wherein adjusting the gain of a depth dependent analog amplification of at least one analog return signal includes adjusting the gain of the depth dependent analog amplification of the at least one analog return signal to at least reduce occurrences of saturation in the analog-to-digital conversion of the at least one analog return signal.

3. The method of claim 1, wherein adjusting the gain of a depth dependent analog amplification of at least one analog return signal includes adjusting the gain of the depth dependent analog amplification of the at least one analog return signal to prevent saturation in the analog-to-digital conversion of the at least one analog return signal.

4. The method of claim 1, wherein monitoring as a function of depth includes, for each of a plurality of ranges of depths setting a status bit in an analog-to-digital conversion saturation status register corresponding to a respective one of the ranges of depths if a saturation monitoring threshold value is encountered or exceeded at the respective one of the ranges of depths for the channel.

5. The method of claim 4 wherein the range of depths is programmable, and further comprising:
    modifying the range of depths for at least some of the channels based on at least one input received from a user.

6. The method of claim 4, further comprising:
    creating a bit mask; and
    applying the bit mask to selectively mask off portions of the analog-to-digital conversion saturation status register corresponding to respective ones of a plurality of transmit focal zones.

7. The method of claim 1, wherein the monitoring is performed as a function of depth and includes, for each of a plurality of ranges of depths incrementing a respective counter for the respective one of the ranges of depths for the channel each time a saturation monitoring threshold is encountered or exceeded at the respective one of the ranges of depths for the channel.

8. The method of claim 1, wherein the monitoring is performed as a function of depth and includes incrementing a respective common counter for the respective one of the ranges of depth each time a saturation monitoring threshold is encountered or exceeded at the respective one of the ranges of depths for any of the channels.

9. The method of claim 1, further comprising:
    setting a saturation threshold based on at least one input received from a user.

10. The method of claim 1, wherein monitoring a digital value resulting from an analog-to-digital conversion for the channel includes determining whether the digital value exceeds at least one of a maximum positive value or a maximum negative value of a respective analog-to-digital converter of the channel.

11. The method of claim 1, further comprising:
    summing a number of digitized return signals of a plurality of channels downstream of the monitoring of the digital values resulting from the analog-to-digital conversion for the channel as a function of depth.

12. The method of claim 1, further comprising providing an alert to a user via a user interface of the ultrasound imaging system.

13. The method of claim 1, wherein adjusting a gain includes adjusting a time gain control profile.

14. The method of claim 1, further comprising providing a confidence metric for at least one automated image measurement.

15. The method of claim 1, further comprising changing a power consumption state of at least a portion of the ultrasound imaging system.

16. The method of claim 1,
wherein adjusting the gain includes adjusting a digital amplification of a digitized return signal resulting from an analog-to-digital conversion of the at least one return signal to compensate for the adjusting of the gain of the depth dependent analog amplification.

17. An ultrasound system, comprising:
an analog amplification stage configured to amplify analog return signals produced by transducer elements that feed a plurality of channels of the ultrasound system in response to echo signals received from a range of depths;
an analog-to-digital conversion stage configured to respectively convert the amplified analog return signals into digital return signals on each of the plurality of channels of the ultrasound system;
an analog-to-digital conversion saturation monitor stage configured to monitor a respective value that is indicative of an analog-to-digital conversion saturation condition for each of the channels as a function of a number of individual depth ranges that are smaller than an entire range of depths from which echo signals are received and to adjust a gain of the analog amplification stage for an individual depth range as a result of detecting a saturation condition in the channel; and
a digital processor stage configured to process the digital return signals.

18. The ultrasound system of claim 17, wherein the analog-to-digital conversion saturation monitor stage is configured to adjust the gain in the analog amplification of the analog return signals produced by the analog amplification stage on each of the plurality of channels of the ultrasound system as a function of depth to at least reduce an occurrence of saturation of the analog-to-digital conversion by the analog-to-digital conversion stage.

19. The ultrasound system of claim 17, wherein the analog-to-digital conversion saturation monitor stage is further configured to adjust the gain in the analog amplification of the analog return signals produced by the analog amplification stage on each of the plurality of channels of the ultrasound system as a function of depth to increase an occurrence of saturation of the analog-to-digital conversion by the analog-to-digital conversion stage.

20. The ultrasound system of claim 17, wherein for each of the channels the analog-to-digital conversion saturation monitor stage is configured to set a status bit in a respective analog-to-digital conversion saturation status register for the channel, the status bit corresponding to a respective one of a plurality of ranges of depths, if a saturation monitoring threshold value is exceeded at the respective one of the ranges of depths for the respective channel.

21. The ultrasound system of claim 20, wherein the analog-to-digital conversion saturation monitor stage is configured to selectively mask off portions of the analog-to-digital conversion saturation status register corresponding to respective ones of a plurality of transmit focal zones with a bit mask.

22. The ultrasound system of claim 17, wherein for each of the channels the analog-to-digital conversion saturation monitor stage is configured to increment a respective counter for a respective one of each of a plurality of ranges of depths each time a saturation monitoring threshold is exceeded at the respective one of the ranges of depths for the respective channel.

23. The ultrasound system of claim 17, wherein the analog-to-digital conversion saturation monitor stage is configured to increment a respective common counter for the respective one of a plurality of ranges of depths each time a saturation monitoring threshold is exceeded at the respective one of the ranges of depths for any of the channels.

24. The ultrasound system of claim 17 wherein the digital processor stage is communicatively coupled to receive a number of compensation signals from the analog-to-digital conversion saturation monitor stage indicative of an amount of compensation to compensate for the adjustment of the gain in the analog amplification of the analog return signals for each of the channels, and is configured to amplify the digital return signals from the analog-to-digital conversion stage for each of the channels based at least in part on the compensation signals.

25. The ultrasound system of claim 17, wherein the analog-to-digital conversion saturation feedback stage is configured to set a saturation monitoring threshold based on at least one input received from a user and modifies a range of depths for at least some of the channels based on at least one input received from a user.

26. The ultrasound system of claim 17 wherein the analog-to-digital conversion saturation monitor stage is configured to cause an alert to be provided via a user interface of the ultrasound imaging system based at least in part on the monitored values.

27. The ultrasound system of claim 17 wherein the analog-to-digital conversion saturation monitor stage is configured to adjust a time gain control profile based at least in part on the monitored values.

28. The ultrasound system of claim 17 wherein the analog-to-digital conversion saturation monitor stage is configured to provide a confidence metric for at least one automated image measurement based at least in part on the monitored values.

29. The ultrasound system of claim 17, wherein the analog-to-digital conversion saturation monitor stage is configured to enter a low power state in response to a lack of saturation and, or, or both enter a normal power state in response to a saturation based at least in part on the monitored values.

30. A subsystem for an ultrasound imaging system, the subsystem comprising:
at least one saturation condition detector configured to detect an analog-to-digital conversion saturation condition in return signals associated with a number of individual depth ranges that are smaller than an entire depth range from which echo signals are received; and
at least one analog amplification adjustor configured to provide at least one adjustment signal to at least one analog amplifier, the at least one adjustment signal indicative of an amount of adjustment in a gain of the amplification of the analog return signals associated with an individual depth range to at least reduce an occurrence of saturation in an analog-to-digital conversion of the analog return signals associated with the individual depth range.

31. The subsystem of claim 30, further comprising:
at least one compensator configured to provide at least one compensation signal to at least one digital amplifier, which at least one compensation signal is indicative of an amount of compensation in an amplification of digitized return signals atoll as compensation for the amount of adjustment in gain in the depth dependent amplification of the analog return signals.

32. The subsystem of claim 31 wherein for each channel the at least one saturation condition detector is configured to, for each of a plurality of ranges of depths, set a status bit in an analog-to-digital conversion saturation status register corresponding to a respective one of the ranges of depths if a saturation monitoring threshold value is encountered or exceeded at the respective one of the ranges of depths for the respective channel.

33. The subsystem of claim 31 wherein for each channel the at least one saturation condition detector is configured to, for each of a plurality of ranges of depths, increment a respective counter for the respective one of the ranges of depths each time a saturation monitoring threshold is encountered or exceeded at the respective one of the ranges of depths for the respective channel.

34. The subsystem of claim 31 wherein the at least one saturation condition detector is configured to increment a respective common counter for the respective one of the ranges of depth each time a saturation monitoring threshold is encountered or exceeded at the respective one of the ranges of depths for any of the channels.

* * * * *